United States Patent [19]
Lock et al.

[11] Patent Number: 5,709,707
[45] Date of Patent: Jan. 20, 1998

[54] SELF-CENTERING UMBRELLA-TYPE SEPTAL CLOSURE DEVICE

[75] Inventors: James E. Lock, Newton; Carol A. Ryan, Lowell; Clifford J. Dwyer, Wilmington, all of Mass.

[73] Assignee: Children's Medical Center Corporation, Boston, Mass.

[21] Appl. No.: 751,371

[22] Filed: Nov. 19, 1996

Related U.S. Application Data

[63] Continuation of Ser. No. 550,215, Oct. 30, 1995, abandoned.

[51] Int. Cl.$^6$ .................................................. A61B 17/00
[52] U.S. Cl. ........................ 606/213; 606/215; 606/151
[58] Field of Search ................................. 606/151, 213, 606/215, 232, 220; 128/887, 889, 899

[56] References Cited

U.S. PATENT DOCUMENTS

| | | |
|---|---|---|
| 3,874,388 | 4/1975 | King et al. |
| 4,007,743 | 2/1977 | Blake . |
| 4,027,677 | 6/1977 | Schulman et al. |
| 4,041,931 | 8/1977 | Eliott et al. |
| 4,112,952 | 9/1978 | Thomas et al. |
| 4,142,531 | 3/1979 | MaGovern . |
| 4,151,012 | 4/1979 | Simkovich et al. |
| 4,519,392 | 5/1985 | Lingua . |
| 4,629,451 | 12/1986 | Winters et al. |
| 4,629,458 | 12/1986 | Pinchuk . |
| 4,706,661 | 11/1987 | Barrett . |
| 4,710,192 | 12/1987 | Liotta et al. |
| 4,741,330 | 5/1988 | Hayhurst . |
| 4,748,982 | 6/1988 | Horzewski . |
| 4,787,388 | 11/1988 | Hofmann . |
| 4,823,794 | 4/1989 | Pierce . |
| 4,826,487 | 5/1989 | Winter . |
| 4,836,204 | 6/1989 | Landymore et al. |
| 4,865,026 | 9/1989 | Barrett . |
| 4,881,939 | 11/1989 | Newman . |
| 4,917,089 | 4/1990 | Sideris . |
| 5,021,059 | 6/1991 | Kensey . |
| 5,052,386 | 10/1991 | Fischer, Jr. . |
| 5,108,420 | 4/1992 | Marks ........................ 606/213 |
| 5,116,357 | 5/1992 | Eberbach . |
| 5,141,515 | 8/1992 | Eberbach . |
| 5,171,259 | 12/1992 | Inoue ........................ 606/213 |
| 5,192,301 | 3/1993 | Kamiya et al. |
| 5,219,359 | 6/1993 | McQuilkin et al. |
| 5,254,133 | 10/1993 | Seid . |
| 5,284,488 | 2/1994 | Sideris ........................ 606/215 |
| 5,334,217 | 8/1994 | Das ............................ 606/213 |
| 5,425,744 | 6/1995 | Fagan et al. ................ 606/151 |
| 5,433,727 | 7/1995 | Sideris ........................ 128/887 |
| 5,451,235 | 9/1995 | Lock et al. .................. 128/899 |

FOREIGN PATENT DOCUMENTS

| | | |
|---|---|---|
| 581995 | 12/1986 | Australia . |
| 1146228 | 5/1983 | Canada . |
| 2057018 | 10/1991 | Canada . |
| 159753 | of 0000 | European Pat. Off. . |
| 0 474 887 A1 | 3/1992 | European Pat. Off. . |
| 0 541 063 A2 | 5/1993 | European Pat. Off. . |
| 2641692 | 7/1990 | France . |
| 2822603 | 11/1979 | Germany . |

(List continued on next page.)

OTHER PUBLICATIONS

Bridge, et al., "Transcatheter Closure of Patient Foramen Ovale after Presumed Paradoxical Embolism", *Circulation*, vol. 86, No. 6, Dec. 1992, pp. 1902–1908.

(List continued on next page.)

*Primary Examiner*—John G. Weiss
*Assistant Examiner*—Bruce E. Snow
*Attorney, Agent, or Firm*—Testa, Hurwitz & Thibeault, LLP

[57] ABSTRACT

A self-centering umbrella-type septal closure device which includes a proximal and distal occluder each having a plurality of arms supporting the occlusion shells. Each of the proximal and distal support arms have at least three coils any one or more of which is secured by a centering mechanism so as to control the positioning of the closure device so that it is centered about a defect.

22 Claims, 5 Drawing Sheets

FOREIGN PATENT DOCUMENTS

| | | |
|---|---|---|
| 3116462 | 12/1982 | Germany . |
| 42 22 291 | 1/1994 | Germany . |
| 57-24132 | 4/1982 | Japan . |
| 1169419 | of 0000 | United Kingdom . |
| WO90/14796 | 12/1990 | WIPO . |
| 9310714 | 5/1993 | WIPO ................................. 606/213 |
| WO 93/13712 | 7/1993 | WIPO . |

OTHER PUBLICATIONS

Cubberly, et al. (ED) "Stainless Steels, Tool Materials and Speacial Purpose Metals" *Metals Handbook*, 9th ed, vol. 3, 1980, p.213, col. 2, last paragraph–col. 3, paragraph 1.

*ELGILOY Brochure*, Jun. 24, 1959, pp. 3–25.

Frick (ED) "Woldman's Engineering Alloys" 1990, *ASM International*, Ohio, p. 425, col. 1, last paragraph (Note differing tensinile and yield strength values).

Ruttenberg, Herbert "Nonsurgical Therapy of Cardiac Disorders", *Pediatric Consultant*, vol. 5, No. 2, 1986.

Sims and Hagel (ED) "The Superalloys" 1972, *Wiley Series of the Science and Technology of Materials*, Section on heat treatment, pp. 161–165.

Bard, Inc. "American College of Physician Executives Recognizes Transcatheter Defect Repair Group", *USCI News*, Sep. 1992, p. 1.

Bridge, et al., "Baffle Fenestration with Subsequent Transcatheter Closure: Modification of the Fontan Operation for Patients at Increased Risk", *Circulation*, vol. 82, No. 5, Nov. 1990,pp. 1681–1689.

Hellenbrand, et al., "Transesophageal Echocardiographic Guidance of Transcatheter Closure of Arterial Septal Defect", *The American Journal of Cardiology*, Jul. 15, 1990, pp. 207–213.

Khan, Ali, et al. "Percutaneous Catheter Closure of the Ductus Arteriosus in Children and Young Adults", *American Journal of Cardiology*, Jul. 15, 1989, pp. 218–221.

Lock, James, et al. "Transcatheter Closure of Arterial Septal Defects", *Circulation*, vol. 79, No. 5, May 1989,pp. 1081–1099.

Rashkind, William, et al. "Congenital Heart Disease, Nonsurgical Closure of Patent Ductus Arteriosus: Clinical Application of the Rashkind PDA Occluder System", *Circulation*, vol. 75, No. 3, Mar. 1987, pp. 583–592.

Rome, John, et al. "Double Umbrella Closure of Arterial Defects", *Circulation*, vol. 82, No. 3, Sep. 1990, pp. 751–758.

SELF-CENTERING UMBRELLA-TYPE SEPTAL CLOSURE DEVICE

This is a continuation of application Ser. No. 08/550,215 filed on Oct. 30, 1995 now abandoned.

FIELD OF THE INVENTION

The invention relates to a self-centering umbrella-type septal closure device which is provided with a support structure having a plurality of arms to support each of the proximal and distal occlusion shells. Each of the proximal and distal support arms has at least three coils any one or more of which is secured by a centering means so as to control the positioning of the closure device within and over a defect and permit the use of a smaller size device for a given defect.

BACKGROUND OF THE INVENTION

The human heart is divided into four compartments or chambers. The left and right atria are located in the upper portion of the heart and the left and right ventricles are located in the lower portion of the heart. The left and right atria are separated from each other by a muscular wall, the intraatrial septum, while the ventricles are separated by the intraventricular septum.

Either congenitally or by acquisition, abnormal openings, holes or shunts can occur between the chambers of the heart or the great vessels, causing shunting of blood through the opening. Such deformities are usually congenital and result from the incomplete formation of the septum, or wall, between chambers during fetal life when the heart forms from a folded tube into a four chambered, two unit system. These deformities can cause significant problems. Ultimately, the ill effects of these defects cause added strain on the heart which may result in heart failure if the defects are not corrected.

Steps have been taken to correct such defects. Prior to recent developments relating to the occlusion of septal defects, extensive surgery was required. The first transcatheter occlusion of patent ductus arteriosus was performed by Posner (in Germany) by transarterially utilizing an Ivalon foam plug. Since that time, this method has been used primarily by German and Japanese investigators in adult and older children. However, this procedure requires a large femoral artery for entry and is known to have significant arterial complications. Consequently, various attempts have been made to close intraatrial defects without surgery.

Prior to the present invention, several defect closure devices have been proposed for closing off intracardiac shunts as an alternative to surgical closure. For example, in U.S. Pat. No. 3,874,388, King et al. disclose an umbrella-like closure device to cover both sides of a shunt defect. Specifically, the device comprises a pair of opposed umbrella-like elements that can be snap-locked together in face-to-face relationship to occlude a defect. Each of the umbrella-like elements includes supporting struts attached to a central hub in a manner permitting the struts to pivot from a position substantially parallel to the central axis of the umbrella-like elements to a position substantially perpendicular to the central axis. Material such as polyester, PTFE, nylon, silastic, pericardium or silk is mounted on the struts and acts to occlude the septal defect once the device has been opened and positioned. Barbs are located on the tips of the struts to engage the septal wall around the defect and maintain the position of the device relative to the defect.

U.S. Pat. No. 4,007,743 to Blake describes another umbrella-like shunt closure device. The Blake '743 patent discloses a device having a series of foldable sections positioned between each of the umbrella arms. The sections automatically open the arms once the device is pushed out and is free of the catheter. Like the King device, Blake requires that the umbrella-like closure elements be snap-locked to each other in vivo.

U.S. Pat. No. 4,917,089 to Sideris relates to a device and process for the occlusion of intracardiac defects. Two independent components are connected across the defect by a button-type closure. The closure apparatus comprises an occluder positioned on the distal side of the defect and an occluder-holder positioned on the proximal side of the defect.

All of these designs are difficult to position and deploy. This is especially a problem with a device having barbs. With such a device, an initial misplacement can result in potentially disastrous consequences because such a device can not generally be repositioned.

Early clamshell occlusion devices were typically much larger than the defect. Such a configuration was utilized to ensure that the defect was covered and to compensate for slippage between the occlusion members at the location of the defect.

Larger occlusion devices, however, may not fit within the heart chamber without interfering with other anatomical parts, particularly valves. Additionally, larger devices are subjected to higher stress levels within the atrial chamber, resulting in a greater potential for fractures of the occlusion device due to fatigue loading. Such occurs because larger devices are forced further from the septal wall due to the curvature of the walls of the atrial chamber.

In view of the limitations of the prior art structures discussed above, a smaller, improved occlusion device is needed. The present invention provides such a device.

SUMMARY OF THE INVENTION

It is therefore an object of the present invention to provide an umbrella-type septal closure device which can self-center within and over a defect.

Another object of the present invention is to provide an umbrella-type septal closure device that is less than twice the size of the defect to be closed.

It is also an object of the present invention to provide an umbrella-type septal closure device which can be effectively used when it is about 1.2 to about 1.8 times the size of the defect to be closed.

A further object of the present invention is to provide an umbrella-type septal closure device that will remain centered within a defect after the device has been introduced and minimize misalignment of the occluders relative to the defect.

These and other objects are achieved by the present invention which provides an umbrella-type septal closure device which can self-center within a defect. The device includes a proximal occluder having a plurality of arms supporting an occlusion shell, a distal occluder having a plurality of arms supporting an occlusion shell, and a centering mechanism secured to at least one of the proximal occluder support arms and to at least one of the distal occluder support arms to center the proximal and distal occluders about a defect.

Other objects, advantages, and salient features of the invention will become apparent from the following detailed description, which taken in conjunction with the annexed drawings, discloses the preferred embodiments of the present invention.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION OF THE DRAWINGS

The invention is directed to a self-centering umbrella-type septal closure device. The self-centering mechanism employed in the present invention controls the positioning of the septal closure device so that the device will be centered about a defect and thereby prevent the occluder members of the closure device from being misaligned across the defect. The centering mechanism of the present invention also allows for the use of umbrella-type septal closure devices that are as small as about 1.2 to about 1.8 times the size of the defect, thus reducing the mechanical stress levels after deployment in the atrial chambers, the risk of fracturing the support arms of the occluder device due to fatigue loading, and the chances for interference with other cardiac structures.

Generally, the umbrella-type self-centering septal closure device comprises a proximal occluder, a distal occluder and a centering structure secured to both the proximal occluder and the distal occluder to control the positioning of the proximal and distal occluders so that they are centered about a defect. The centering structure includes at least one centering member secured to the proximal and distal occluders.

Several embodiments of the present invention are discussed below. Each embodiment is discussed in conjunction with the same type of septal closure device, namely the umbrella-type occluder which is disclosed in U.S. Pat. No. 5,425,744 owned by the assignee of the present invention, said patent being incorporated herein by reference. The umbrella-type occluder includes two umbrella-like occlusion members attached at a center point. Each umbrella is supported by at least three outwardly extending arms preferably having three or more resilient coils radially spaced from the center point. Resilient coils are preferred because they are less likely to fracture due to fatigue loading; and they allow the occluder to be temporarily deformed in order to fit into a deployment mechanism.

Figure 11:
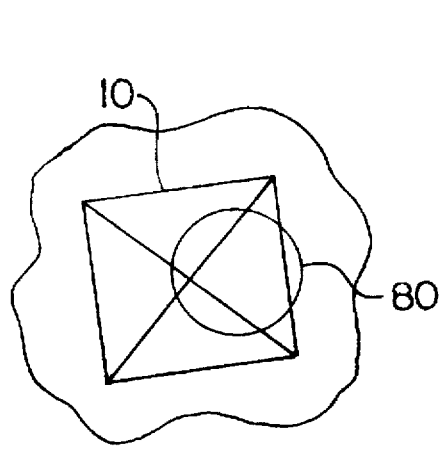
FIG. 11 is a top schematic view of a septal closure device without the centering device of the present invention in a defect.

When the umbrella-type occluder is used without the centering device of the present invention, the occluders must be accurately sized to approximately twice the diameter of the defect (approximately 1.8–2.8 for atrial septal defects) as measured angiographically with a sizing balloon. As shown in FIG. 11, the primary reason for sizing the occluders to about twice the size of the defect, is the inability of the occluders to center within the defect. While the umbrella-type occluder may be useful for small defects, larger defects (>20 mm.) must be closed surgically due to limitations associated with existing device sizes.

It should be noted that while the centering device of the present invention is discussed in conjunction with a particular umbrella-type occluder device such discussion is for illustration only and does not limit the scope of the invention which may be used with other umbrella-type occluders.

As shown in FIGS. 1–10, septal occluder 10 comprises a proximal occluder 12 and a distal occluder 14, and includes an overall support structure 16 for supporting a generally square proximal occlusion shell 18 and a square distal occlusion shell 20. The support structure is preferably manufactured from MP35N® alloy sold by the Carpenter Steel Division of Carpenter Technology, located in Reading, Pa., or Maryland Specialty Wire, Inc., located in Cockeysville, Md. The MP35N® alloy is a non-magnetic, nickel-cobalt-chromium-molybdenum alloy having high tensil strength, good ductility and corrosion resistance. The alloy which conforms to the American Society for Testing and Materials' F562 standard, has the elemental composition as shown in Table 1. The shells may be preferably constructed from a knitted polyester fabric. The shells are each sewn as at 22, with a polyester suture, to the facing sides of proximal support structure 24 and distal support structure 34.

Figure 1:
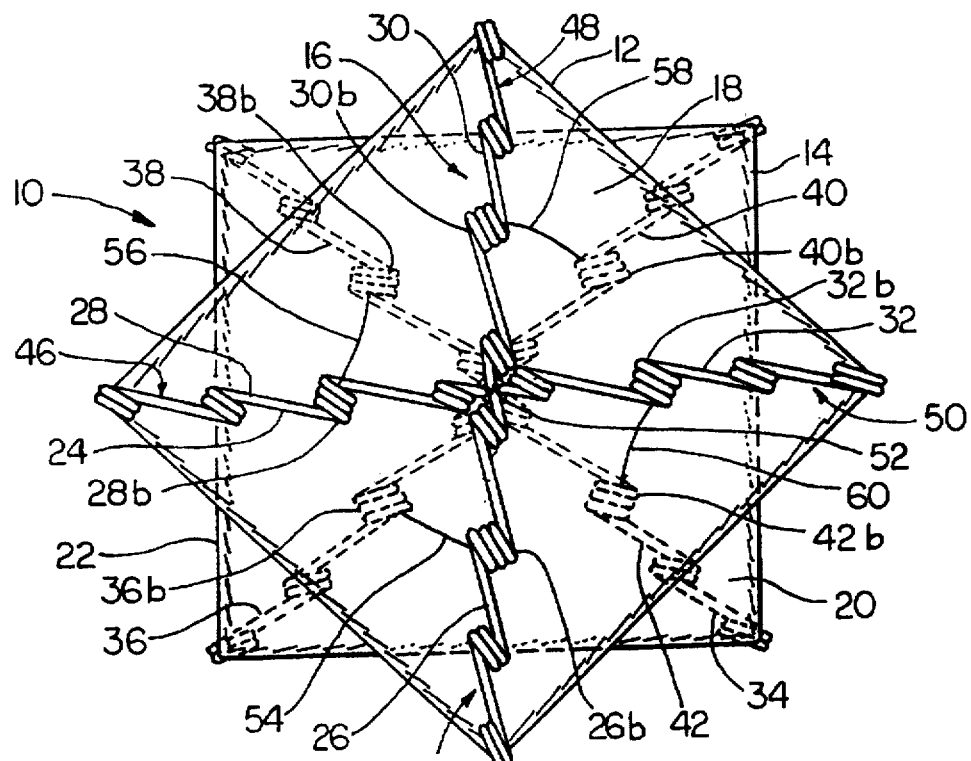
FIG. 1 is a top plan view of a first embodiment.

Each of the proximal and distal support structures includes at least three outwardly extending arms. FIG. 1 shows the proximal support structure 24 having four outwardly extending arms 26, 28, 30, and 32 and the distal support structure 34 similarly having four outwardly extending arms 36, 38, 40, and 42. Each outwardly extending arm is resiliently biased and preferably includes, in one embodiment, a shoulder coil 26a, an elbow coil 26b, a wrist coil 26c, and a suture coil 26d.

The overall support structure 16 is constructed from four spring arm subassemblies 44, 46, 48, and 50. As a result, two arms are formed from a single piece of metal. Specifically, first proximal arm 26 and first distal arm 36, second proximal arm 28 and second distal arm 38, third proximal arm 30 and third distal arm 40, and fourth proximal arm 32 and fourth distal arm 42 are respectively subassemblies 44, 46, 48, and 50. In one embodiment, the four subassemblies can be mechanically secured together by wire 52 with adjacent subassemblies offset by 90°. Other means such as laser welding can be used to secure the four subassemblies together.

While the preferred embodiment discloses an occlusion device that is square, other shapes may be utilized without departing from the spirit of the present invention. Additionally, while each arm of the occluder is resiliently biased as a result of the shoulder, elbow, and wrist coils, other resilient structures could be utilized in constructing the framework for the occlusion shells.

Figure 2:
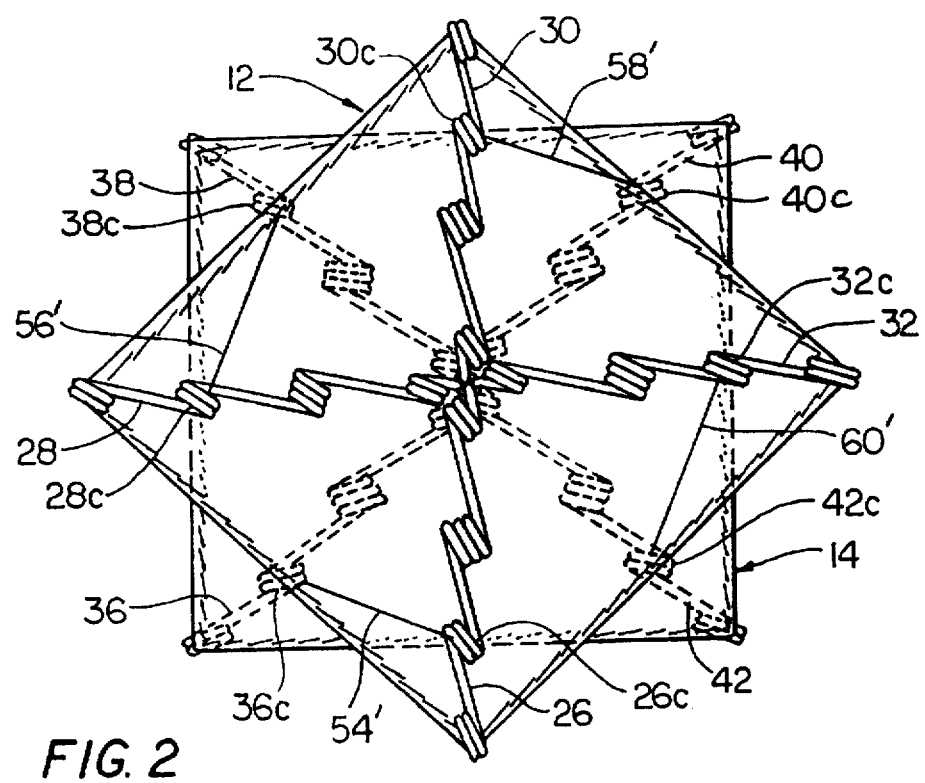
FIG. 2 is a top plan view of an alternate version of the first embodiment.
Figure 3:
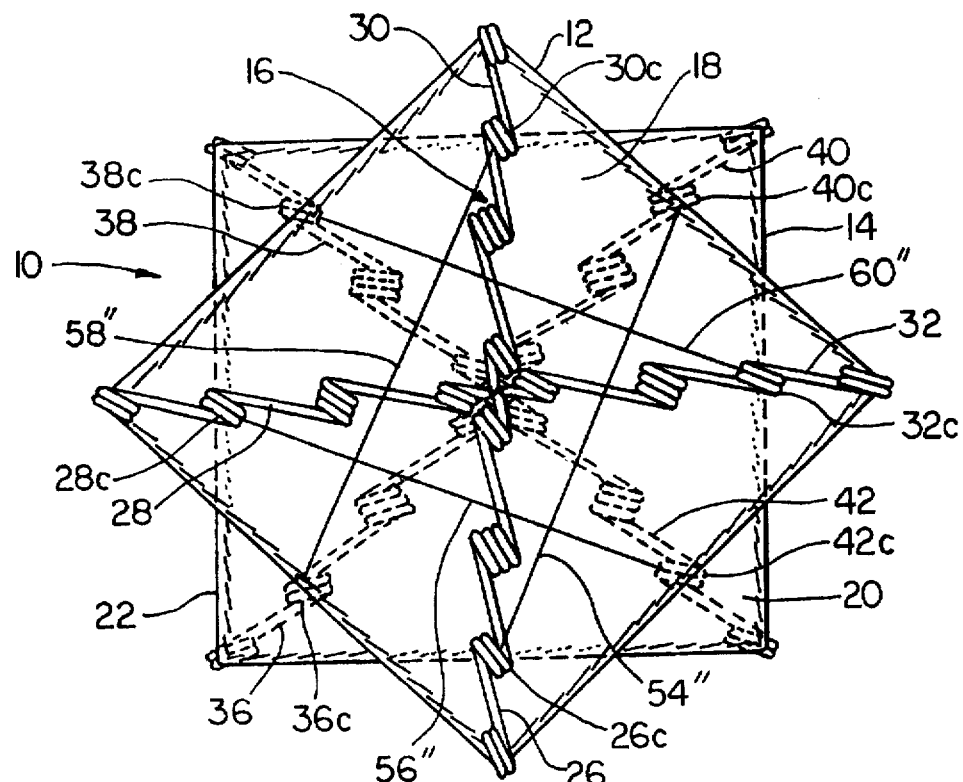
FIG. 3 is a top plan view of a further version of the first embodiment.

With reference to FIGS. 1 through 3 the first embodiment of the present invention is disclosed. As stated previously, septal occluder 10 includes proximal occluder 12 with four arms that are opened on one side of a defect and distal occluder 14 with four arms that are opened on the other side of the defect. The first embodiment provides four centering members 54, 56, 58, and 60 secured between the arms of the proximal and distal occluders. The centering members 54, 56, 58, and 60 may be made of elastomeric, biocompatible polymeric materials. The centering members preferably have the properties of long term biocompatability, toughness, resiliency, high elongation and ease of processing into a monofilament. Potential materials for the centering members include natural rubber (latex) or various thermoplastic elastomers such as Hytrel (PBT/PEO block copolymers), PEBA (polyether amide block copolymers), or SBS (styrene butadiene styrene)/SEBS (styrene ethylene butadiene styrene) block copolymers.

Three connection patterns for the centering members are shown in FIGS. 1–3, although other connection patterns are possible without departing from the spirit and scope of the present invention. With reference to FIG. 1, centering members 54, 56, 58, and 60 are secured to elbow coils of adjacent distal arms and proximal arms. Specifically, a first centering member 54 is connected between the elbow coil 26b of the first proximal arm 26 and the elbow coil 36b of the first distal arm 36, a second centering member 56 is connected between the elbow coil 28b of the second proximal arm 28 and the elbow coil 38b of the second distal arm 38, a third centering member 58 is connected between the elbow coil 30b of the third proximal arm 30 and the elbow coil 40b of the third distal arm 40, and a fourth centering member 60 is connected between the elbow coil 32b of the fourth proximal arm 32 and the elbow coil 42b of the fourth distal arm 42.

Another connection pattern is shown in FIG. 2, where the centering members 54', 56', 58', and 60' are secured between the wrist coils of adjacent proximal and distal arms. Specifically, a first centering member 54' is connected between the wrist coil 26c of the first proximal arm 26 and the wrist coil 36c of the first distal arm 36, a second centering member 56' is connected between the wrist coil 28c of the second proximal arm 28 and the wrist coil 38c of the second distal arm 38, a third centering member 58' is connected between the wrist coil 30c of the third proximal arm 30 and the wrist coil 40c of the third distal arm 40, and a fourth centering member 60' is connected between the wrist coil 32c of the fourth proximal arm 32 and the wrist coil 42c of the fourth distal arm 42.

FIG. 3 illustrates a third connection pattern, with the centering members 54", 56", 58", and 60" being connected between wrist coils of diametrically opposed proximal arms and distal arms. Specifically, a first centering member 54" is connected between the wrist coil 26c of the first proximal arm 26 and the wrist coil 40c of the third distal arm 40, a second centering member 56" is connected between the wrist coil 28c of the second proximal arm 28 and the wrist coil 42c of the fourth distal arm 42, a third centering member 58" is connected between the wrist coil 30c of the third proximal arm 30 and the wrist coil 36c of the first distal arm 36, and a fourth centering member 60" is connected between the wrist coil 32c of the fourth proximal arm 32 and the wrist coil 38c of the second distal arm 38. Attachment between wrist coils of diametrically opposed proximal and distal arms minimizes the stretching of the centering members during loading of the occluder into the delivery system, although the degree of centering may be somewhat decreased.

Figure 4:
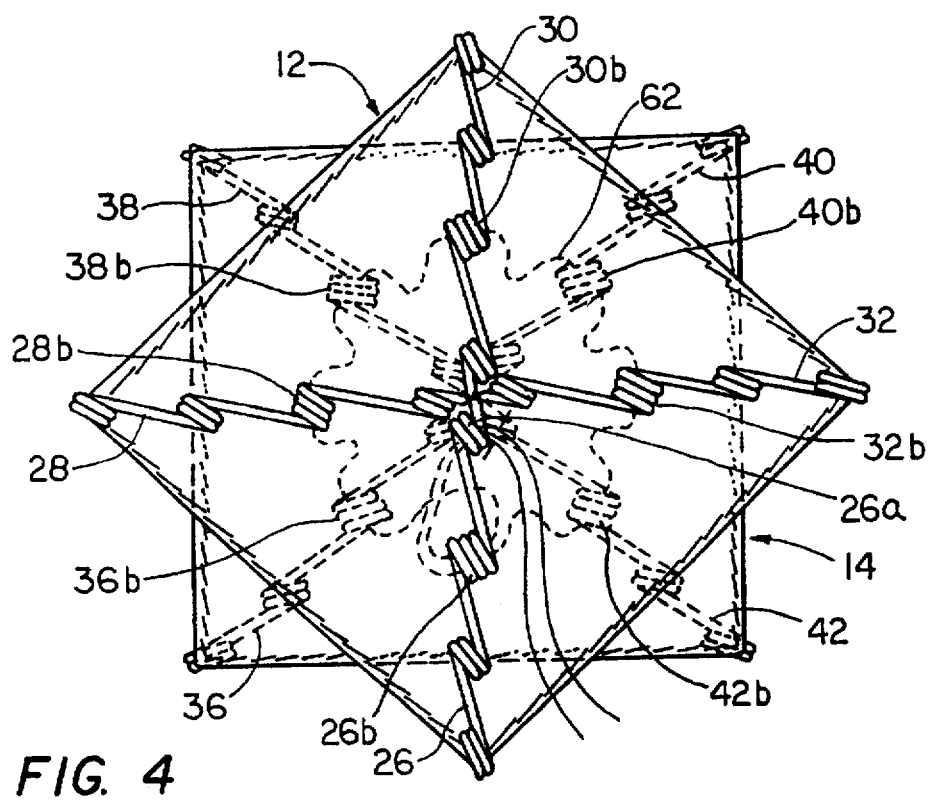
FIGS. 4 and 5 are top plan views of a second embodiment.
Figure 5:
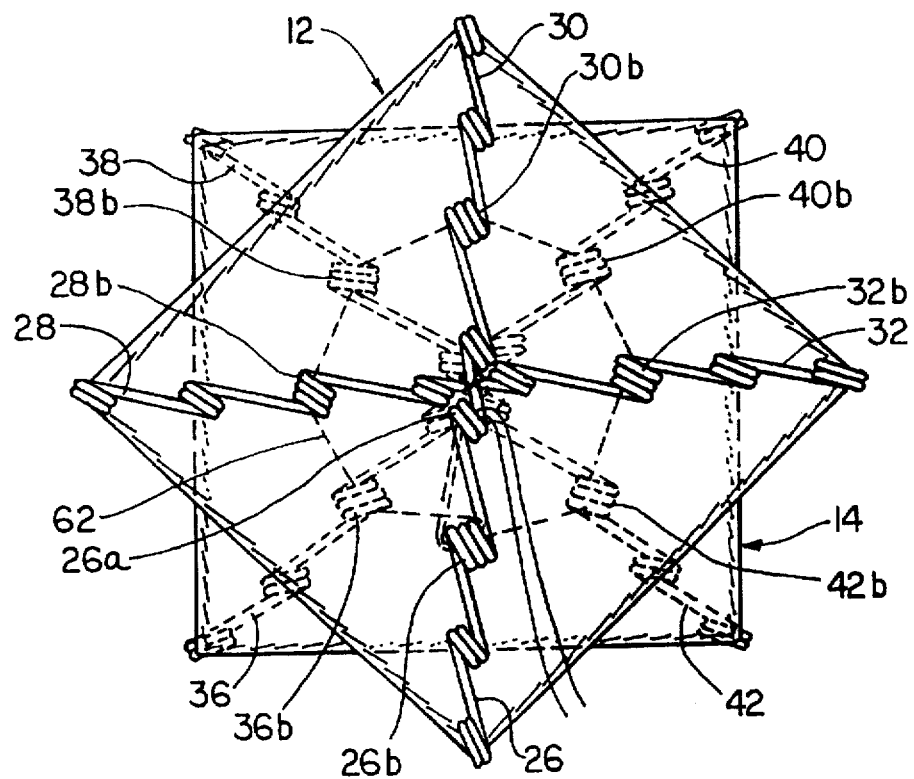

With reference to FIGS. 4 and 5, a second embodiment of the present invention is shown. Briefly, the second embodiment utilizes a centering suture 62 threaded through the coils of the proximal and distal arms of the septal occluder 10. In accordance with the second embodiment, a self-centering septal closure device is produced by threading the centering suture 62 through shoulder coil 26a of the first proximal arm 26 and subsequently threading the centering suture 62 through the elbow coil 26b of the first proximal arm 26. The suture 62 is then threaded through the elbow coil 36b of the first distal arm 36. The procedure is continued, alternately threading the suture 62 through the elbow coils of the proximal and distal arms until the suture 62 is looped through the elbow coil 26b of the first proximal arm 26 for a second time. At this point, the suture 62 is threaded through the shoulder coil 26a of the first proximal arm 26 for a second time, and both ends of the suture are accessible from the proximal side. FIG. 4 shows the device with the centering suture fully relaxed, while FIG. 5 shows the suture in a tensioned state.

Another threading pattern that can be used to produce a self-centering septal closure device involves threading the centering suture 62 through shoulder coil 26a of the first proximal arm 26 and subsequently threading the centering suture 62 through the wrist coil 26c of the first proximal arm 26. The suture 62 is then threaded through the wrist coil 36c of the first distal arm 36. The procedure is continued, alternately threading the suture 62 through the wrist coils of the proximal and distal arms until the suture 62 is looped through the wrist coil 26c of the first proximal arm 26 for a second time. At this point, the suture 62 is threaded through the shoulder coil 26a of the first proximal arm 26 for a second time, and both ends of the suture are accessible from the proximal side.

Referring again to the first threading pattern of the second embodiment discussed above, once the occluders are placed across the defect, the suture can be pulled to eliminate the slack between the elbow coils. This creates a larger centered diameter. As a result, the likelihood of the device moving off center is minimized. The centering suture can be adjusted to accommodate odd shaped defects. This can be accomplished with the use of a slip knot or one-way knot. Once the suture is pulled to eliminate the slack, the centering suture can be trimmed off by mechanical means. It should be noted that while two threading patterns have been disclosed, it may be possible to utilize other threading patterns without departing from the spirit and scope of the present invention.

A third embodiment of the present invention is shown in FIGS. 6, 7, 8 and 9. According to the third embodiment, four centering members made of either a polymer or metal shape memory material are connected between the proximal arms 26, 28, 30, and 32 and distal arms 36, 38, 40, and 42. FIGS. 6 through 9 show the centering members connected between wrist coils of adjacent proximal arms and distal arms in the same pattern as shown with regard to the second connection pattern of the first embodiment (see FIG. 2), although other connection patterns such as those shown in FIGS. 1 and 3 could be used without departing from the spirit of the present invention.

Figure 6:
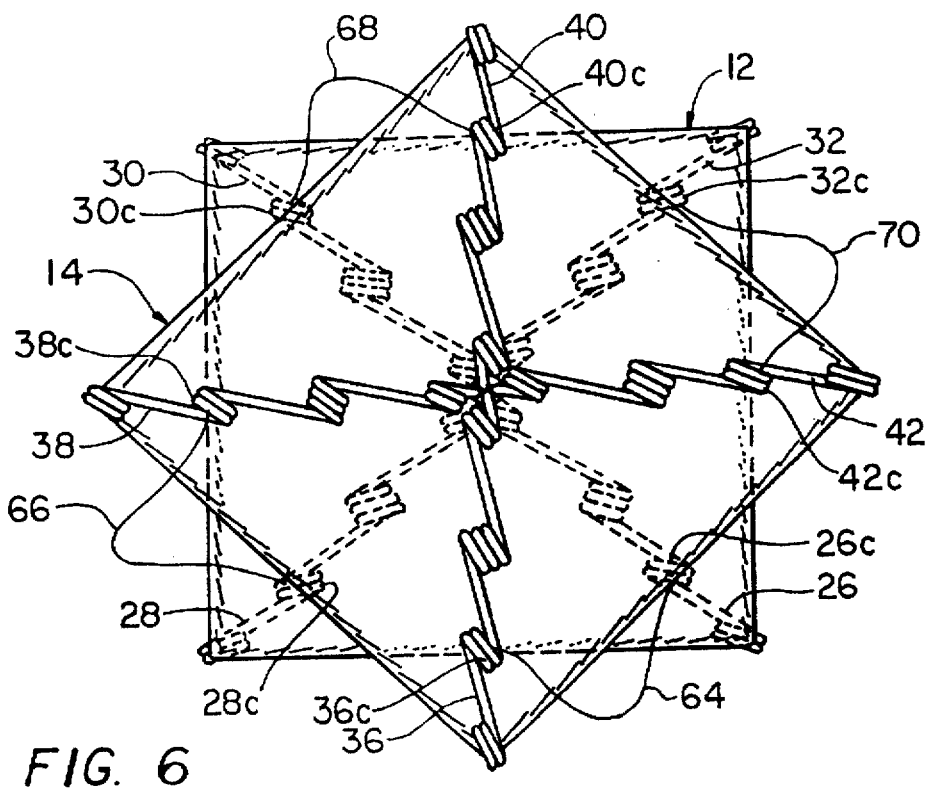
FIG. 6 is a top plan view of a third embodiment.
Figure 7:
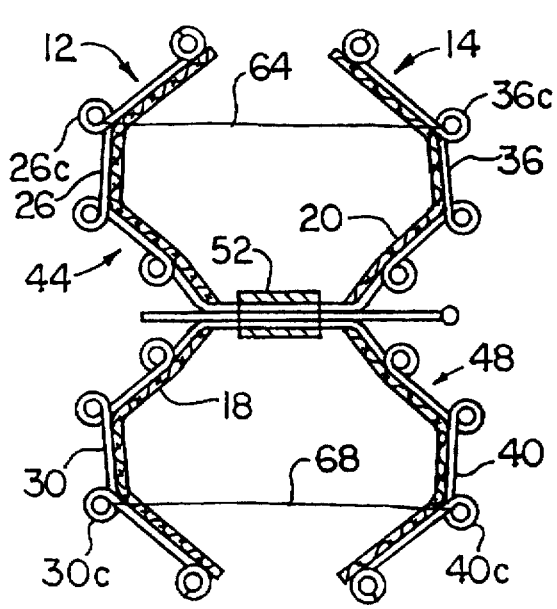
FIG. 7 is a cross-sectional view of the third embodiment.

The centering members 64, 66, 68, and 70 shown in FIGS. 6 and 7 are made of polymer shape memory materials. Polymer shape memory materials deform because of stretching during loading of the device and then return to their prior shape after exposure to body temperature. Alternatively, the centering members can be polymer shape memory materials which are initially long enough for loading into a delivery system (with no force required to stretch) and which shrink after exposure to body temperature inside the patient.

Figure 8:
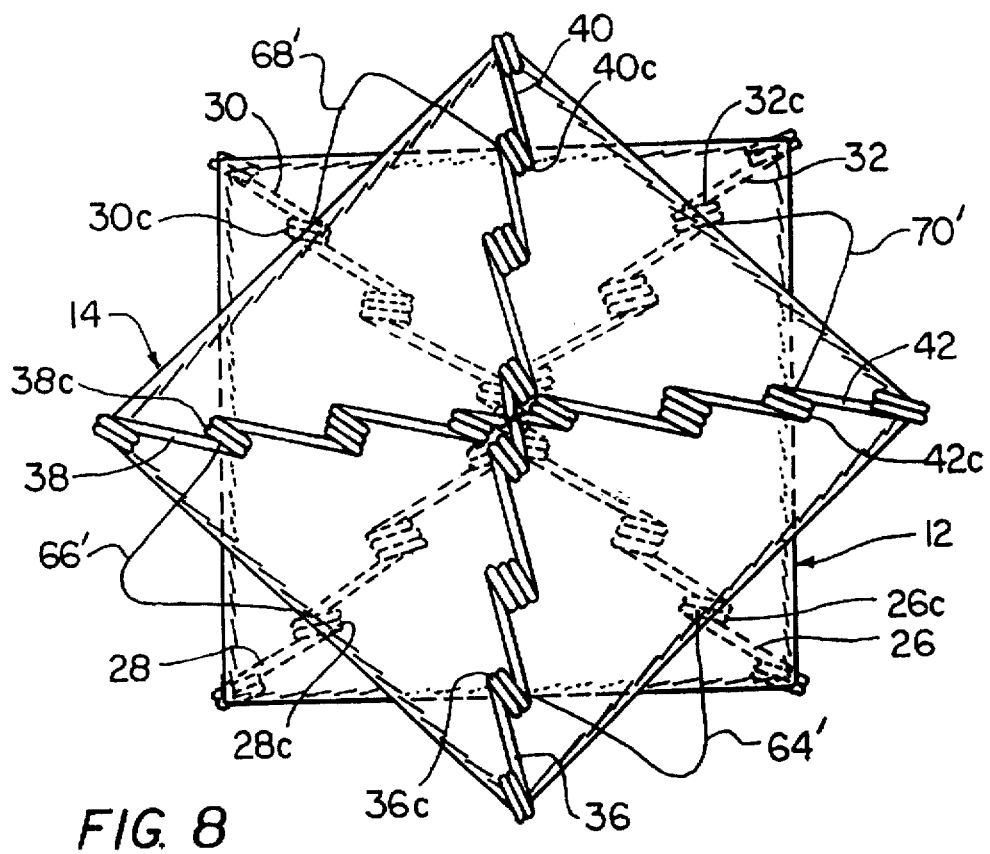
FIG. 8 is a top plan view of an alternate version of the third embodiment.
Figure 9:
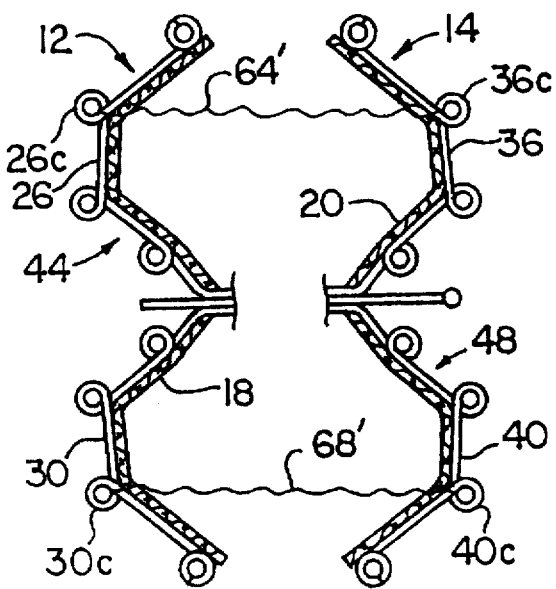
FIG. 9 is a cross-sectional view of the alternate version of the third embodiment.

Another variation on the use of shape memory materials is shown in FIGS. 8 and 9, where the centering members 64', 66', 68', and 70' are pieces of small diameter wire made from a shape memory metal, such as Ni—Ti (nitinol). The connecting members may be secured between the wrist coils of adjacent proximal arms and distal arms in the same pattern as shown with respect to the second connection pattern of the first embodiment (See FIG. 2) although other connection patterns could be used. The centering members 64', 66', 68', and 70' are set to reform into a shorter wire upon exposure to body temperature within the patient. This version is advantageous in that it requires no force to deform during loading, has a low profile and good frictional properties, and is less prone to damage during loading.

Figure 10:
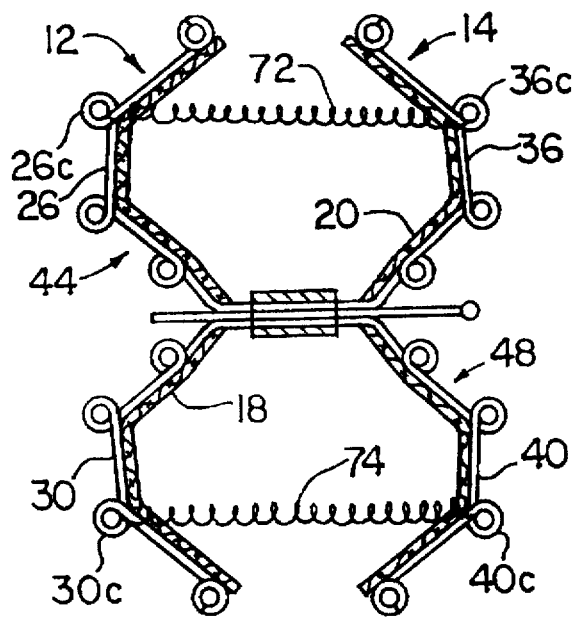
FIG. 10 is a cross-sectional view of a fourth embodiment.

A fourth embodiment is shown in FIG. 10. As with the first embodiment, the fourth embodiment uses four resilient centering members 72, 74 (two are not shown) secured between the proximal arms 26, 28, 30, and 32 and the distal arms 36, 38, 40, and 42. In contrast to the first embodiment, the centering members of the fourth embodiment are metal (or plastic) springs secured between the wrist coils of adjacent proximal arms and distal arms. Specifically, the centering members are secured between wrist coils of adjacent proximal arms and distal arms in the same pattern as shown with regard to the second connection pattern of the first embodiment (see FIG. 2), although other connection patterns could be used without departing from the spirit of the present invention.

Use of a plastic or metal spring still requires the application of force to stretch the spring during loading, but there is the advantage of having the flexibility to use various materials for the spring including MP35N® from which the occluder framework is fabricated.

Metallic embodiments three and four simplify finding materials with physical properties and biocompatability for long term implantation. Additionally, since the materials used in embodiments three and four are likely to be closer in stiffness to the arms of the occluder, it is unlikely that the force required to stretch the filaments could damage the occluder arms. Finally, embodiments three and four may be helpful in limiting the overall profile of the device when it is loaded into the delivery system. This would result in lowering the loading friction of the device.

Each of the preferred embodiments are self-centering umbrella-type septal closure devices, which greatly reduce the size of the occluders necessary to properly close a defect. This is accomplished by the centering members which form an outer boundary preventing the septal closure device from moving substantially off-center within a defect.

Figure 12:
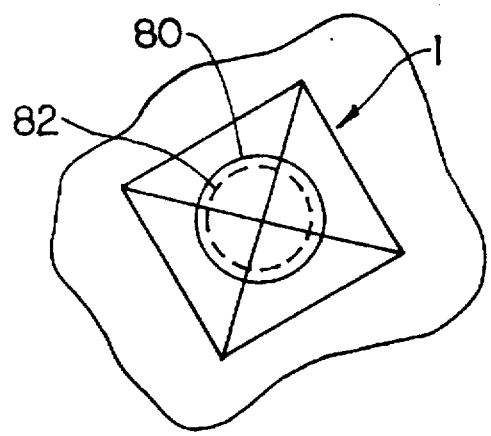
FIG. 12 is a top schematic view of the septal closure device of the present invention centered about a defect.

With reference to FIGS. 11 and 12, a septal closure device 10 without the centering members and one of the present septal closure devices 1 is shown, respectively. With reference to FIG. 11, the septal closure device 10 has a wide range of movement about the defect 80, and can easily move off-center. In contrast, the centering member(s) of the present septal closure device 1 (FIG. 12) create a boundary 82 which retains the septal closure device 1 about the center of the defect 80.

The centering septal occluder 10 is deployed in the same manner as other occluders. A sheath is first inserted into the defect as performed by one skilled in the art. The occluder 10 is then loaded into a catheter, which is inserted through the sheath. The distal occluder 14 of the occluder 10 is released into the distal heart chamber through the sheath. The sheath and catheter are then pulled back into the proximal heart chamber, where the proximal occluder 12 of the device 10 is deployed. Once deployed, centering members, generally, 54, 56, 58, and 60 contact the edges of the defect, centering the device 10 in the defect. Once correct position is confirmed, the device 10 is released from the catheter and the catheter is withdrawn.

While the preferred embodiments of the present invention have been shown and described, it should be understood that it is intended to cover all modifications and alternate methods falling within the spirit and scope of the invention as defined in the appended claims or their equivalents.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the following claims.

TABLE 1

| Carbon | 0.025% max |
|---|---|
| Manganese | 0.15% max |
| Silicon | 0.15% max |
| Phosphorus | 0.015% max |
| Sulfur | 0.010% max |
| Chromium | 19.00/21.00% |
| Nickel | 33.00/37.00% |
| Molybdenum | 9.00/10.50% |
| Cobalt | Balance |
| Titanium | 1.00% max |
| Boron | 0.010% |
| Iron | 1.00% max |

What is claimed is:

1. A septal defect closure device, comprising:
a proximal occluder including a plurality of outwardly extending proximal arms supporting a proximal occlusion shell;
a distal occluder including a plurality of outwardly extending distal arms supporting a distal occlusion shell; and
a centering mechanism secured between said proximal occluder and said distal occluder to center said proximal and said distal occluders about a defect, said centering mechanism comprising at least two centering members, each of said centering members secured between a separate one of said proximal arms and a corresponding one of said distal arms, at least one of said centering members comprising an elastomeric material.

2. The closure device according to claim 1, wherein each of said at least two centering members is secured between a separate one of said proximal arms and an adjacent one of said distal arms.

3. The closure device according to claim 1, wherein each of said at least two centering members is secured between a separate one of said proximal arms and a diametrically opposed one of said distal arms.

4. The closure device according to claim 1, wherein said at least one elastomeric centering member is secured between one of said proximal arms and an adjacent one of said distal arms.

5. The closure device according to claim 1, wherein said at least one elastomeric centering member is secured between one of said proximal arms and a diametrically opposed one of said distal arms.

6. The closure device according to claim 1, wherein each of said proximal arms includes a resilient shoulder coil adjacent the center point of said proximal occluder, a resilient elbow coil radially spaced from said shoulder coil and a resilient wrist coil radially spaced from said elbow coil and each of said distal arms includes a resilient shoulder coil adjacent the center point of said distal occluder, a resilient elbow coil radially spaced from shoulder coil and resilient wrist coil radially spaced from said elbow coil.

7. The closure device according to claim 6, where said elastomeric centering member is passed through said proximal and distal shoulder coils and said proximal and distal elbow coils to center said proximal occluder and said distal occluder about a defect.

8. The closure device according to claim 6, wherein said proximal occluder and said distal occluder each include at least three outwardly extending arms, said elastomeric centering member being first passed through said shoulder coil of a first proximal arm and subsequently threaded through said elbow coil of said first proximal arm, said elastomeric centering member then being passed through said elbow coil of an adjacent distal arm and threaded alternately through said elbow coils of said remaining proximal and distal arms until said elastomeric centering member is looped through said elbow coil of said first proximal arm for a second time, then passing said suture centering member through said shoulder coil of said first proximal arm for a second time leaving both ends of said elastomeric centering member accessible.

9. The closure device according to claim 6, wherein said elastomeric centering member is passed through said shoulder coils and said wrist coils to center said proximal occluder and said distal occluder about a defect.

10. The closure device according to claim 6, wherein said proximal occluder and said distal occluder each include at least three outwardly extending arms, said elastomeric centering member being first passed through said shoulder coil of a first proximal arm and subsequently threaded through said wrist coil of said first proximal arm, said elastomeric centering member then being passed through said wrist coil of an adjacent distal arm and threaded alternately through said wrist coils of said remaining proximal and distal arms until said elastomeric centering member is looped through said wrist coil of said first proximal arm for a second time, then passing said suture centering member through said shoulder coil of said first proximal arm for a second time leaving both ends of said elastomeric centering member accessible.

11. A septal defect closure device, comprising:
  a proximal occluder including a plurality of outwardly extending proximal arms supporting a proximal occlusion shell;
  a distal occluder including a plurality of outwardly extending distal arms supporting a distal occlusion shell; and
  a centering mechanism secured between said proximal occluder and said distal occluder to center said proximal and said distal occluders about a defect, said centering mechanism comprising at least two centering members, each of said centering members secured between a separate one of said proximal arms and a corresponding one of said distal arms, at least one of said centering members comprising a spring.

12. The closure device according to claim 11, wherein said at least one spring centering member is secured between one of said proximal arms and an adjacent one of said distal arms.

13. The closure device according to claim 11, wherein said at least one spring centering member is secured between one of said proximal arms and a diametrically opposed one of said distal arms.

14. The closure device according to claim 11, wherein each of said at least two centering members is secured between a separate one of said proximal arms and a diametrically opposed one of said distal arms.

15. The closure device according to claim 11, wherein each of said at least two centering members is secured between a separate one of said proximal arms and an adjacent one of said distal arms.

16. A septal defect closure device, comprising:
  a proximal occluder including a plurality of outwardly extending proximal arms supporting a proximal occlusion shell;
  a distal occluder including a plurality of outwardly extending distal arms supporting a distal occlusion shell; and
  a centering mechanism secured between said proximal occluder and said distal occluder to center said proximal and said distal occluders about a defect, said centering mechanism comprising at least two centering members, each of said centering members secured between a separate one of said proximal arms and a corresponding one of said distal arms, at least one of said centering members comprising a shape memory material.

17. The closure device according to claim 16, wherein said proximal arms extend outwardly from said proximal occluder center point to support said proximal occlusion shell and said distal arms extend outwardly from said distal occluder center point to support said distal occlusion shell and wherein
  said at least one memory material centering member is secured between one of said proximal arms and one of said distal arms at a position radially spaced from said proximal and distal occluder center points.

18. The closure device according to claim 17 where said one of said proximal arms is adjacent said one of said distal arms.

19. The closure device according to claim 17 wherein said one of said proximal arms is diametrically opposed to said one of said distal arms.

20. A method of repairing a septal defect comprising the steps of:
  (a) providing the septal defect closure device of claim 1;
  (b) positioning said distal occluder and said proximal occluder on different sides of said septal defect; and
  (c) opening said distal occluder and said proximal occluder such that each of said proximal and distal occluders occlude said septal defect.

21. A method of repairing a septal defect comprising the steps of:
  (a) providing the septal defect closure device of claim 11;
  (b) positioning said distal occluder and said proximal occluder on different sides of said septal defect; and
  (c) opening said distal occluder and said proximal occluder such that each of said proximal and distal occluders occlude said septal defect.

22. A method of repairing a septal defect comprising the steps of:
  (a) providing the septal defect closure device of claim 16;
  (b) positioning said distal occluder and said proximal occluder on different sides of said septal defect; and
  (c) opening said distal occluder and said proximal occluder such that each of said proximal and distal occluders occlude said septal defect.

* * * * *